US006264700B1

(12) United States Patent
Kilcoyne et al.

(10) Patent No.: US 6,264,700 B1
(45) Date of Patent: Jul. 24, 2001

(54) PROSTHETIC GASTROESOPHAGEAL VALVE

(75) Inventors: John Kilcoyne; Brian S. Kelleher, both of San Diego, CA (US)

(73) Assignee: Endonetics, Inc., San Diego, CA (US)

( * ) Notice: Subject to any disclaimer, the term of this patent is extended or adjusted under 35 U.S.C. 154(b) by 0 days.

(21) Appl. No.: 09/140,935

(22) Filed: Aug. 27, 1998

(51) Int. Cl.[7] ........................................ A61F 2/36
(52) U.S. Cl. ............................ 623/23.68; 623/23.7
(58) Field of Search ...................... 623/12, 2, 23.64, 623/23.65, 23.67, 23.68, 23.7, 23.76, 23.74, 23.72; 604/4

(56) References Cited

U.S. PATENT DOCUMENTS

| 15,192 | 6/1856 | Pearle . |
|---|---|---|
| 3,898,701 | * 8/1975 | La Russa .................................. 3/1.5 |
| 3,926,175 | 12/1975 | Allen et al. . |
| 4,204,282 | 5/1980 | Bolt . |
| 4,218,782 | 8/1980 | Rygg . |
| 4,265,694 | 5/1981 | Boretos et al. . |
| 4,271,828 | 6/1981 | Angelchick . |
| 4,403,604 | 9/1983 | Wilkinson et al. . |
| 4,417,360 | 11/1983 | Moasser . |
| 4,451,936 | 6/1984 | Carpentier et al. . |
| 4,605,407 | 8/1986 | Black et al. . |
| 4,642,105 | 2/1987 | Toter . |
| 4,705,516 | * 11/1987 | Barone et al. ........................... 623/2 |
| 4,735,607 | 4/1988 | Keith, Jr. . |
| 4,747,849 | 5/1988 | Galtier . |
| 4,759,757 | 7/1988 | Pinchuk . |
| 4,759,758 | 7/1988 | Gabbay . |
| 4,763,653 | 8/1988 | Rockey . |
| 4,778,461 | 10/1988 | Pietsch et al. . |
| 4,790,843 | * 12/1988 | Carpentier et al. ....................... 623/2 |
| 4,796,603 | 1/1989 | Dahlke et al. . |
| 4,846,836 | * 7/1989 | Reich ....................................... 623/11 |
| 5,006,106 | 4/1991 | Angelchik . |
| 5,019,102 | 5/1991 | Hoene . |
| 5,084,061 | 1/1992 | Gau et al. . |
| 5,314,473 | * 5/1994 | Godin ..................................... 623/12 |
| 5,411,552 | * 5/1995 | Andersen et al. ........................ 623/2 |
| 5,549,666 | * 8/1996 | Hata et al. .............................. 623/2 |
| 5,733,337 | 3/1998 | Carr, Jr. et al. . |
| 5,782,916 | * 7/1998 | Pintauro et al. ........................ 623/12 |
| 5,792,094 | * 8/1998 | Stevens et al. ........................... 604/4 |
| 5,840,081 | 11/1998 | Andersen et al. . |
| 5,861,036 | * 1/1999 | Godin ..................................... 623/12 |
| 5,957,949 | * 9/1999 | Leonhardt et al. ..................... 606/194 |

FOREIGN PATENT DOCUMENTS

| 0 233 102 A1 | 8/1987 | (EP) . |
|---|---|---|
| 2 513 111 | 9/1981 | (FR) . |
| 2 069 339 A | 8/1981 | (GB) . |
| 4-212348 | 8/1992 | (JP) . |
| 1635980 A1 | 3/1991 | (SU) . |
| WO 91/01117 | 2/1991 | (WO) . |
| WO 96/29954 | 10/1996 | (WO) . |

* cited by examiner

Primary Examiner—David H. Willse
Assistant Examiner—Alvin Stewart
(74) Attorney, Agent, or Firm—Knobbe, Martens, Olson & Bear, LLP (57) ABSTRACT

Disclosed is a prosthetic gastroesophageal valve assembly, for transesophageal implantation to treat gastroesophageal reflux disease. The valve assembly includes an anchor for attachment to the wall of the esophagus and a valve permanently or removably connected to the anchor. Related devices and methods are also disclosed.

16 Claims, 6 Drawing Sheets

PROSTHETIC GASTROESOPHAGEAL VALVE

BACKGROUND OF THE INVENTION

This invention relates to a prosthetic valve for non-invasive insertion in the vicinity of the lower esophagus sphincter (LES).

Gastroesophageal reflux is a physical condition in which stomach acids reflux, or flow back up from the stomach into the esophagus. Frequent reflux episodes (two or more times per week), results in a more severe problem known as gastroesophageal reflux disease (GERD). Gastroesophageal reflux disease is the most common form of dyspepsia, being present in approximately 40% of adults in the United States or an intermittent basis and some 10% on a daily basis. Dyspepsia or heartburn, is defined as a burning sensation or discomfort behind the breastbone or sternum and is the most common symptom of GERD. Other symptoms of gastroesophageal reflux disease include dysphasia, odynophagia, hemorrhage, water brash, and pulmonary manifestations such as asthma, coughing or intermittent wheezing due to acid aspiration. Dyspepsia also may mimic the symptoms of a myocardial infarction or severe angina pectoris.

Factors that are believed to cause GERD include: transient lower esophageal sphincter relaxations, decreased LES resting tone, delayed stomach emptying, and ineffective esophageal clearance. One primary cause of gastroesophageal reflux disease is the lack of competency of the lower esophageal sphincter. The lower esophageal sphincter or valve, is comprised of both smooth and skeletal muscle located at the gastroesophageal (GE) junction.

At rest, the LES maintains a high-pressure zone between 10 and 30 mm Hg above intragastric pressure. Upon deglutition, the LES relaxes before the esophagus contracts, allowing food to pass through into the stomach. After food passes into the stomach, the LES contracts to prevent the stomach contents and acids from regurgitating into the esophagus. The mechanism of the LES opening and closing is influenced by innervation via the vagus nerve and hormonal control of gastrin and possibly other gastrointestinal hormones.

Complications of GERD include esophageal erosion, esophageal ulcer, and esophageal stricture. Stricture formation often results from prolonged exposure of the esophageal mucosa to acid reflux. The most common clinical manifestation of stricture is dysphasia. Unlike dysphasia from non-strictured esophageal reflux, dysphasia caused by stricture is a progressive disorder in that the size of a bolus which can pass into the stomach progressively becomes smaller. Prolonged acid exposure to esophageal mucosa may lead to a more serious condition known as Barrett's esophagus. Barrett's esophagus is defined as the replacement of normal squamous epithelium with abnormal columnar epithelium. Barrett's esophagus or clinical change in tissue structure is clinically important not only as a marker of severe reflux, but also as a potential precursor to cancer of the esophagus.

Current methods of treating gastroesophageal reflux disease consist of life style changes such as weight loss and avoidance of certain foods that may exacerbate the symptoms of GERD. Avoidance of excessive bending combined with elevation of the head of the bed helps prevent nocturnal reflux. While avoidance of exacerbating factors may be helpful, there is relatively little data supporting the efficacy of lifestyle modification alone for the treatment of GERD. There are a variety of different techniques designed for the treatment of less serious cases of GERD. Medications have been used for years with varying results. Conventional antacids (TUMS®, ROLAIDS®) produce short term relief, but often result in negative side effects including diarrhea and constipation. H2 blocker receptor antagonists (Cimetidine, Ranitidine) are relatively more effective in controlling symptoms than antacids, but result in treatment of the symptoms and not the underlying cause of the disease. The more powerful secretory inhibitors, the proton pump inhibitors (Omeprazole, Lansoprazole) are much more effective than H2 blockers, but are expensive and may, in the long term, produce negative side effects. The only alternative to these conventional forms of medical treatment, which must be taken constantly at great cost, are the surgical methods of preventing reflux.

There are numerous reflux operations available which perhaps reflect the inadequacy of any one procedure to totally control the problem. The most commonly performed operation, Nissen fundoplication, may be effective, but is often complicated by stricture formation or gas bloat syndrome. A laparoscopic Nissen approach has been developed, adding another dimension of difficulty, with long term results still in question. In addition, a percutaneous laparoscopic technique has been developed as can be seen, for example, in the U.S. Pat. No. 5,006,106 to Angelchik. Minimally invasive techniques, such as transesophageal implantation of a prosthetic valve have been attempted. See, for example, U.S. Pat. No. 4,846,836 to Reich. The existing forms of medical and surgical treatment for gastroesophageal reflux all have shortcomings.

In view of the foregoing, and notwithstanding the various efforts exemplified in the prior art, there remains a need for a non-invasive prosthetic valve and deployment methodology for transesophageal implantation into the vicinity of the lower esophageal sphincter. Preferably, the valve permits both antegrade and retrograde flow and is removable or replaceable with minimal trauma to the surrounding tissue.

SUMMARY OF THE INVENTION

There is provided in accordance with one aspect of the present invention a prosthetic gastroesophageal valve for implantation in the vicinity of the lower gastroesophageal sphincter. The valve comprises a flexible anchor, having a proximal end, a distal end, and a lumen extending therethrough. A valve is provided on the anchor. The anchor comprises a tissue ingrowth surface thereon, for contacting the esophagus and permitting cellular ingrowth therein. In one embodiment, the anchor comprises a tubular polymeric membrane such as PTFE.

In accordance with another aspect of the present invention, there is provided a method of attaching a prosthesis to the esophagus. The method comprises the steps of providing a prosthesis having at least one cellular ingrowth surface thereon, and preparing a surface of the wall of the esophagus for attachment to the cellular ingrowth surface. The cellular ingrowth surface is brought into contact with the prepared surface of the esophagus, and cellular ingrowth is permitted from the wall of the esophagus into the cellular ingrowth surface to attach the prosthesis to the wall of the esophagus.

The preparing the surface of the wall of the esophagus step comprises injuring a portion of the surface of the wall of the esophagus, such as by mechanical abrasion, chemical treatment, application of RF energy, or other technique. In one embodiment, the prosthesis comprises a valve. The valve may be either permanently attached to the cellular ingrowth surface or removably attached to the cellular ingrowth surface.

Preferably, the cellular ingrowth surface comprises a layer of porous material such as PTFE. The layer may be a tubular sheet of PTFE or other porous material, or a tubular structure having a laminate of porous cellular ingrowth permitting material on the radially outwardly facing surface thereof and one or more layers of different material or less porous material on the radially inwardly facing surface thereof.

In one aspect of the method, the step of permitting cellular ingrowth from the wall of the esophagus into the cellular ingrowth surface to attach the prosthesis to the wall of the esophagus further includes the step of positioning an expandable support within the esophagus to press the cellular ingrowth surface against the wall of the esophagus.

In accordance with a further aspect of the present invention, there is provided a method of treating gastroesophageal reflux disease. The method comprises the steps of providing a prosthetic gastroesophageal valve, having a tubular anchor and a valve thereon. The valve assembly may be transesophageally, laparoscopically or percutaneously positioned at about the base of the esophagus or the cardia. The anchor is brought into contact with the wall of the esophagus or cardia to permit cellular ingrowth through the wall of the anchor.

In one embodiment, the method further comprises the step of expanding a tubular support within the anchor, to press the anchor against the wall of the esophagus. Preferably, the method further comprises the step of removing the tubular support from the anchor following a cellular ingrowth period of time. The cellular ingrowth period of time is generally in excess of about one or two days, typically more than about six or eight days, and generally less than about six weeks.

Further features and advantages of the present invention will become apparent from the detailed description of preferred embodiments which follow, when considered together with the attached drawings and claims.

DETAILED DESCRIPTION OF THE PREFERRED EMBODIMENT

Figure 1:
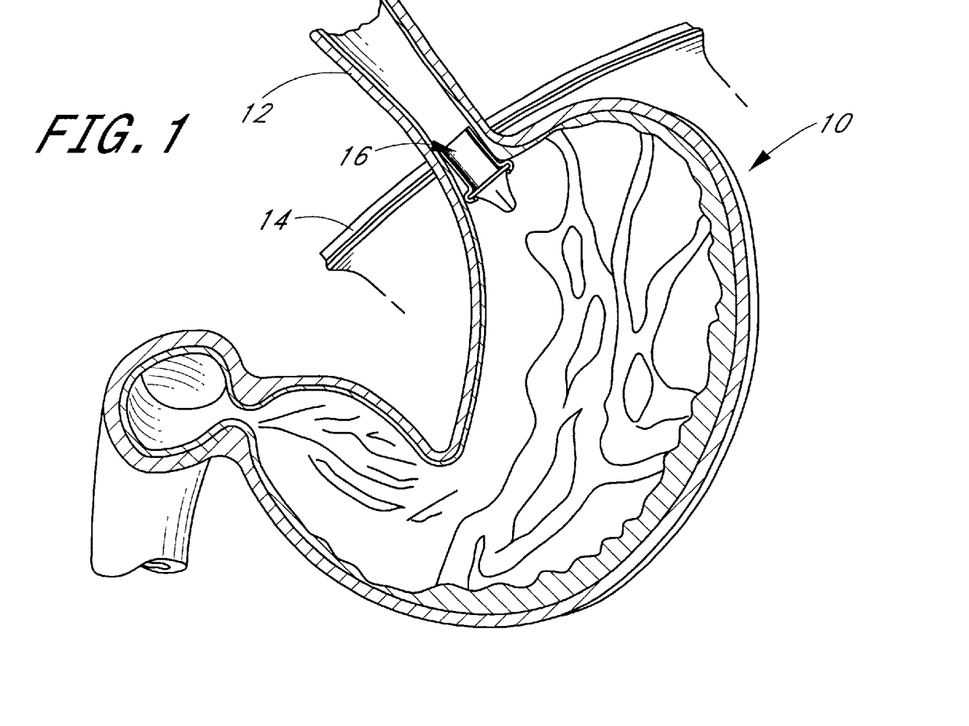
FIG. 1 is a schematic view of a removable gastroesophageal valve assembly in accordance with the present invention, positioned at about the junction between the esophagus and the stomach.

Referring to FIG. 1, there is illustrated a schematic representation of the stomach 10 and a portion of the lower esophagus 12. The esophagus 12 extends through the diaphragm 14, below which the esophagus 12 communicates with the interior of the stomach 10. A prosthetic gastroesophageal valve assembly 16 in accordance with the present invention is illustrated at about the junction between the lower esophagus 12 and the stomach 10.

Although the anatomy illustrated in FIG. 1 is generally normal, except for the improperly functioning native lower gastroesophageal sphincter, the present invention is also useful in patients having lower esophageal abnormalities, such as a hiatal hernia. In this condition, a portion of the wall of the stomach 10 extends upwardly through the diaphragm 14 and herniates superiorly to the diaphragm 14. The existence of a hiatal hernia or other abnormality in the lower esophagus may affect the implanted location of the valve assembly 16, but will generally not disqualify a patient otherwise treatable with the valve assembly 16 of the present invention.

Figure 2:
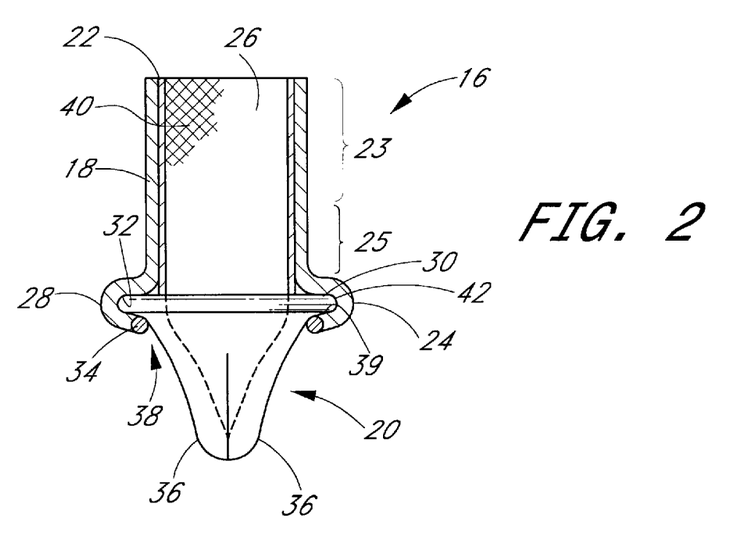
FIG. 2 is a side elevational view of the valve assembly of FIG. 1.

Referring to FIG. 2, the valve assembly 16 generally comprises an anchor 18 and a valve 20. The anchor 18 can comprise any of a variety of structures useful for securing the valve 20 to the lower portion of the esophagus. For example, any of a variety of tubular structures which can be secured to the esophagus or cardia through the use of hooks, pins, sutures, adhesives, staples, clips, tacks and/or radially outwardly directed force can be used. Alternatively, any of a variety of non-tubular structures, such as axially extending attachment strips or connectors, can be utilized to attach the valve assembly 20 to the esophageal wall or cardia. Such attachment strips can be secured to the esophageal wall or other internal anatomical structure using any of a variety of connectors, such as hooks, pins, sutures, adhesives, staples, tacks, clips and others which will be apparent to those of skill in the art.

In a preferred embodiment, however, the anchor 18 comprises a flexible tubular sleeve adapted to permit cellular ingrowth to provide the primary long term fixation against both proximal and distal axial movement. Suitable materials include polytetrafluoroethylene, polyethylene terephthalate, polyester, polyurethane, silicone and other materials which will be apparent to those of skill in the art in view of the present disclosure. As used herein, "distal" shall refer to a location closer to the stomach and "proximal" shall refer to a location closer to the mouth.

The anchor 18 is preferably porous to permit cellular ingrowth of the lining of the esophagus to inhibit axial migration. In addition, since ingrowth of the mucosal lining in one embodiment goes through the sleeve, the resulting anchor will be lined with living tissue. This ingrown cellular layer may also protect the artificial material of the anchor from physical damage due to passing material.

Porosity in the range of from about $2\mu$ to about $100\mu$ or greater may be desirable to facilitate ingrowth. In one embodiment of the invention, the anchor 18 comprises a tubular PTFE extrusion, having a wall thickness of about 0.4 mm, a porosity of about $20\mu$, an axial length of about 1.5 cm, and a diameter of about 2 cm. Suitable dimensions for any particular application can be readily determined by those of ordinary skill in the art in view of the disclosure herein.

The anchor 18 is generally characterized by a proximal end 22, a distal end 24 and a lumen 26 extending therethrough. Preferably, the lumen is substantially free of obstructions, to optimize the cross-section of the esophageal flow path. The axial length of the anchor 18 is divided into two functional components. A proximal attachment zone 23 is sufficiently long to permit attachment between the anchor 18 and the esophagus. The length of the attachment zone 23 may vary depending upon the attachment mode. For example, a relatively shorter attachment zone 23 may be utilized where supplemental attachment structures such as sutures, hooks, pins, staples, tacks, clips or adhesives are intended to be left in place to retain the valve assembly 16 within the lower esophagus or cardia. Alternatively, a relatively longer attachment zone 23 may be desirable where cellular ingrowth is the primary or exclusive long-term mode of attachment. In general, an axial length of the attachment zone 23 will typically be greater than about 1 cm, preferably greater than about 1.5 cm, and may be greater than about 2 cm in an embodiment intended to be restrained by cellular ingrowth.

A distal portion of the anchor 18 includes a flexible skirt portion 25, for extending between the attachment portion 23 and a valve or a releasable connector 28. The skirt portion 25 permits a flexible connection between the attachment portion 23 of the anchor which is secured to the esophageal wall or cardia and the releasable connector 28 which is secured to the valve 20. The skirt portion also permits suspending the valve in the stomach, if desired. Flexibility in the skirt between the valve 20 and the attachment point to the esophagus or cardia desirably accommodates natural movement (i.e., radial contraction and expansion) of the esophagus or cardia as well as any residual native esophageal sphincter function, without compromising the attachment between the anchor 18 and the wall of the esophagus or cardia. The use of a flexible tubular skirt portion of at least about 1 cm and preferably 2 cm or more in length is believed to permit reciprocal contraction and expansion of the lower esophagus from diameters as large as 20 mm or more down to substantially closed without disrupting the cellular ingrowth or other attachment at the attachment zone 23.

The valve 20 may be either permanently or releasably connected to the anchor 18. Permanent attachment can be accomplished in a variety of ways such as by integrally forming the valve 20 with the anchor 18. Alternatively, a separately formed valve 20 can be attached to the anchor 18 using adhesives and/or mechanical attachment structures such as sutures, clips, metal loops or other interference fit or mechanical junctions.

The distal end 24 of the anchor 18 is alternatively provided with a releasable connector 28 in a releasable valve embodiment. Preferably, the valve 20 is provided with a corresponding proximal connector 30 which contains a complementary surface structure to the releasable connector 28 on the distal end 24 of anchor 18. In the illustrated embodiment, the releasable connector 28 comprises a radially outwardly extending annular recess 32 having a greater internal cross-sectional area than the cross-sectional area of the distal aperture 38 at the distal end of the releasable connector 28. In this manner, the proximal connector 30 on valve 20 can be resiliently deformed (e.g., compressed) to fit through the distal aperture 38 and expand within the annular recess 32, thereby providing a removable interference fit between the valve 20 and the anchor 18. The foregoing structure advantageously also permits both the implantation of the valve within the releasable connector 28 and removal of the valve from the releasable connector 28 either proximally through the central lumen 26 of anchor 18 or distally through the distal aperture 38.

In the embodiment illustrated in FIG. 2, an annular restraining loop 34 is molded within or attached to the wall of the distal end 24 of anchor 18, to resist or limit radial expansion of the distal aperture 38. Loop 34 may comprise any of a variety of materials, such as metal wire, suture, mono-filament or multi-filament polymeric fibers, and the like, as will be appreciated by those of skill in the art in view of the disclosure herein. Loop 34 may be molded within a distal portion 24 of the anchor 18, or attached thereto such as by sutures, adhesives, weaving through the material of anchor 18, or other techniques known in the art. Loop 34 may also be merely a thickened section of the wall of anchor 18. In general, the inside diameter of aperture 38 and consequent diameter of loop 34 is selected to cooperate with the outside diameter of proximal connector 30 to provide a sufficient interference fit to permit implantation and extraction of the valve 20 from the releasable connector 28 as desired, but resist proximal or distal movement of the valve 20 with respect to the anchor 18 under normal anatomical forces.

In one embodiment of the present invention, the anchor 18 has an inside diameter within the range of from about 15 mm to about 20 mm, and the distal aperture 38 has an inside diameter at least about 5% and preferably as much as 10% or more smaller than the inside diameter of the anchor 18. This provides one or more interference surfaces 39 facing generally in the proximal direction for providing an interference fit with the valve 20. The interference surface 39 is preferably an annular surface, surrounding the aperture 38. Interference surface 39 may face in a proximal direction, or be radially outwardly inclined in the proximal direction as illustrated. Alternatively, interference surface 39 may be provided along a series of discrete elements circumferentially spaced around the aperture 38.

The proximal connector 30 of valve 20 has a maximum diameter which is preferably at least about 1 or 2 mm greater than the diameter of aperture 38 and, more preferably, is at least 3 to 5 mm or more greater in diameter than the diameter of the aperture 38. The proximal connector 30 is configured in a manner that produces an interference surface 42 which either faces in a distal direction, or is inclined radially inwardly in the distal direction as illustrated. In this manner, the interference surface 42 of the proximal connector 30 engages the interference surface 39 on releasable connector 28 to removably restrain the valve 20 within the releasable connector 28.

The extent of the interference necessary to achieve a useful retention force can be readily determined through routine experimentation by one of ordinary skill in the art in view of the materials utilized for the releasable connector 28 and proximal connector 30. For example, a relatively larger interference surface area will be desirable for highly flexible or elastic materials such as silicone. More rigid materials and/or the use of reinforcement structures such as wire loop 34 will enable a smaller total interference surface area as will be apparent to those of skill in the art.

Any of a variety of alternative interference fit or snap fit structures can be adapted for use at the junction between the valve 20 and the anchor 18 as may be desired for a particular application. For example, radially outwardly extending annular flanges on the valve 20 may snap fit within one or more annular recesses on the anchor 18. Alternatively, anchor 18 may be provided with radially inwardly extending projections or annular flanges to be received within a radially inwardly extending slot or slots on the proximal connector 30 of valve 20.

In the illustrated embodiment, the valve 20 comprises one or more proximal connectors 30 and two or more moveable or flexible leaflets 36. Although the present invention will be discussed primarily in terms of a two-leaflet or three-leaflet valve, any of a wide variety of valve structures can be removably coupled to the anchor 18 in accordance with the present invention and accomplish the objectives of the prosthetic gastroesophageal valve. The specific valving mechanism can thus be varied without departing from the spirit of the present invention. In general, the valve 20 preferably has a structure which permits as large as possible an open cross-sectional area so that it will not obstruct the flow of material from the esophagus into the stomach.

In one embodiment, the valve 20 comprises a three-leaflet valve injection molded or otherwise formed from silicone or polyurethane, and containing a tapered wall such that the distal end (coaptive edges) of each leaflet 36 has a lesser wall thickness than the proximal (superior) ends of the leaflets 36. In addition, a thickened annular band is preferably provided in the region of the proximal connector 30, to increase the resistance to radial collapse. One or more internal support structures such as annular wire loops may be integrally molded within or attached to the proximal end of the valve 20 to increase the radial strength of the proximal connector 30. At least one radiopaque marker is also included, to permit visualization as is understood in the art.

Preferably, the valve 20 permits both forward flow from the esophagus into the stomach, as well as limited reverse flow. One structure for enabling controlled reverse flow is upper valve 36 disclosed in U.S. Pat. No. 4,846,836 to Reich, entitled Artificial Lower Gastrointestinal Valve, the disclosure of which is incorporated by reference in its entirety herein. Other provisions for reverse flow will be discussed infra, in connection with FIGS. 4 and 5.

Figure 4A:
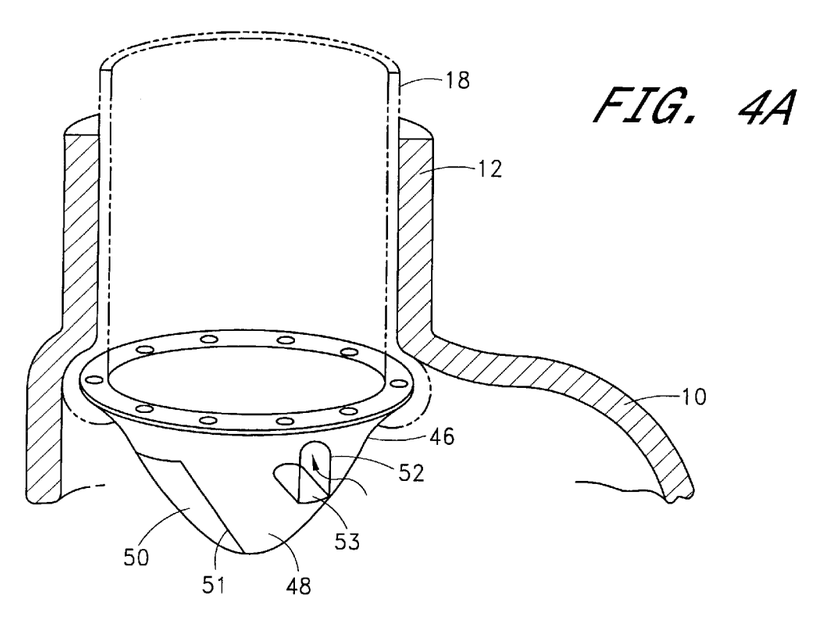
FIGS. 4a and 4b show schematic views of an alternate gastroesophageal valve assembly in accordance with the present invention.
Figure 4B:
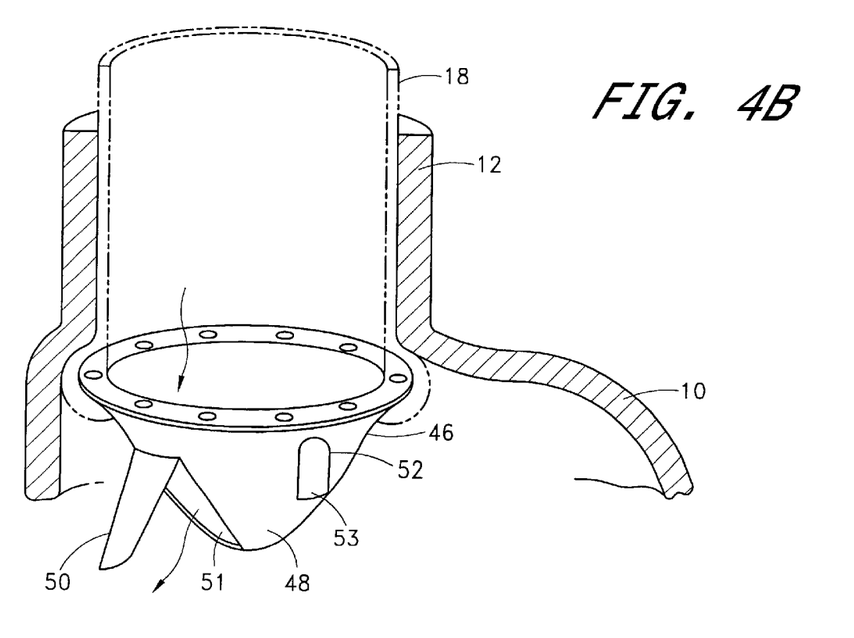

Referring to FIGS. 4a and 4b, there is illustrated an alternate valve 46 permanently or removably secured to an anchor 18 in position within the distal esophagus 12 (or cardia) at about the junction with the stomach 10. The valve 46 comprises a generally conically-shaped body 48 having a forward flow opening 51 and a reverse flow opening 52. The forward flow opening 51 is provided with a movable first valve cover 50 illustrated in a closed orientation in FIG. 4a and in an open orientation in FIG. 4b. The valve cover 50 may be biased towards a closed position to obstruct reverse flow through aperture 51. However, forward flow of material from the esophagus into the stomach displaces the valve cover 50 to permit forward flow.

The reverse flow opening 52 is provided with a second valve cover 53 illustrated in a closed orientation in FIG. 4b. Valve cover 53 will open in response to retrograde pressure in excess of a predetermined break pressure for permitting reverse flow. Although the hinge side of valve cover 53 is illustrated at the lower edge of the reverse flow opening 52, the hinge may alternatively be located at the upper edge of opening 52 similar to the illustrated valve cover 51. Each of the valve covers 51 and 53 may be integrally molded with the housing 48, or separately formed and attached thereto, as may be desired in the view of the preferred manufacturing technique. The entire housing 48 including valve covers 51 and 53 may be injection molded from any of a variety of flexible biocompatible materials such as, for example, silicone or polyurethane. The cross-sectional area of the forward flow aperture 50 and reverse flow aperture 52 can be varied as desired, depending upon the clinical objective.

Figure 3:
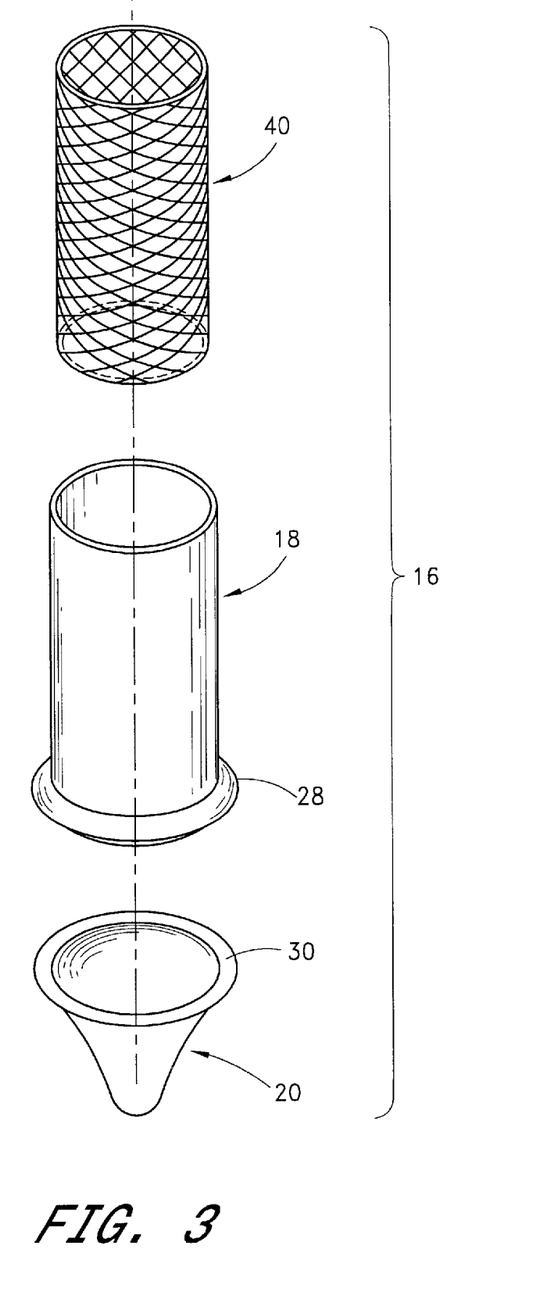
FIG. 3 is an exploded perspective view of the valve, anchor, and temporary tubular support in accordance with one embodiment of the present invention.

In accordance with another embodiment of the present invention (FIG. 7) there is provided a hybrid valve structure which includes both the leaflet primary valve construction of FIGS. 1–3 and the reverse flow valve construction of the embodiment of FIG. 4. Thus, forward flow through the valve is accomplished by forward pressure opening two or three or more coaptive valve leaflets. One or two or three or more of the leaflets are provided with a reverse flow aperture such as aperture 52 in FIG. 4. The reverse flow aperture is additionally provided with a valve cover such as valve cover 53 illustrated in FIG. 4.

Figure 7:
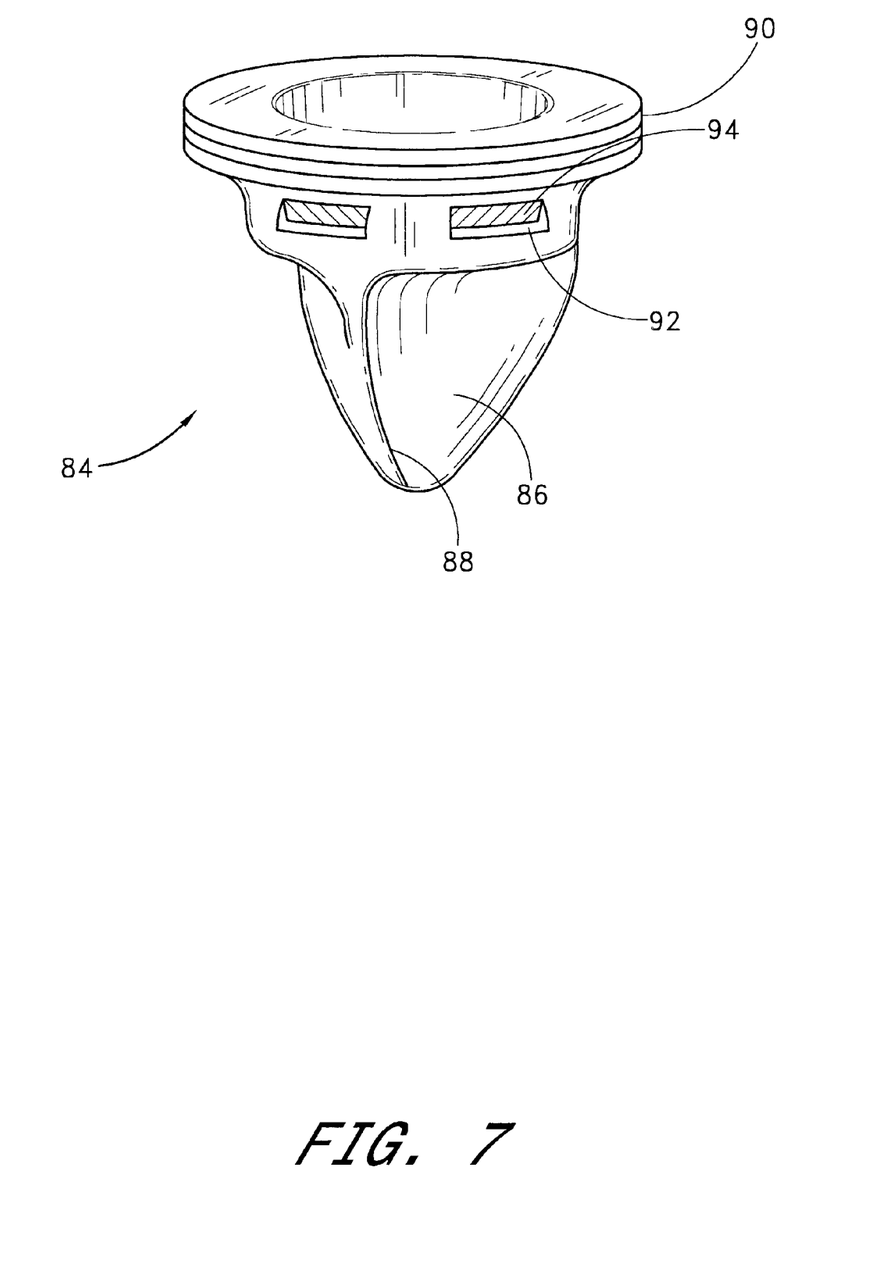
FIG. 7 is a schematic representation of an alternate embodiment of the present invention.

Referring to FIG. 7, valve 84 includes at least two and preferably three leaflets 86, separated by coaptive edges 88 as is well known in the heart valve art. The leaflets 86 are connected to a base 90, which may be permanently or removably connected to an anchor as has been discussed. Alternatively, the coaptive leaflets 86, base 90 and anchor (not illustrated) can be intregally formed as a unitary device. One or more reverse flow ports 92 are provided on valve 84. Preferably, two or three or more reverse flow ports 92 are provided. Each reverse flow port is provided with a valve cover 94, for inhibiting forward flow but permitting reverse flow through the flow port 92.

Figure 5:
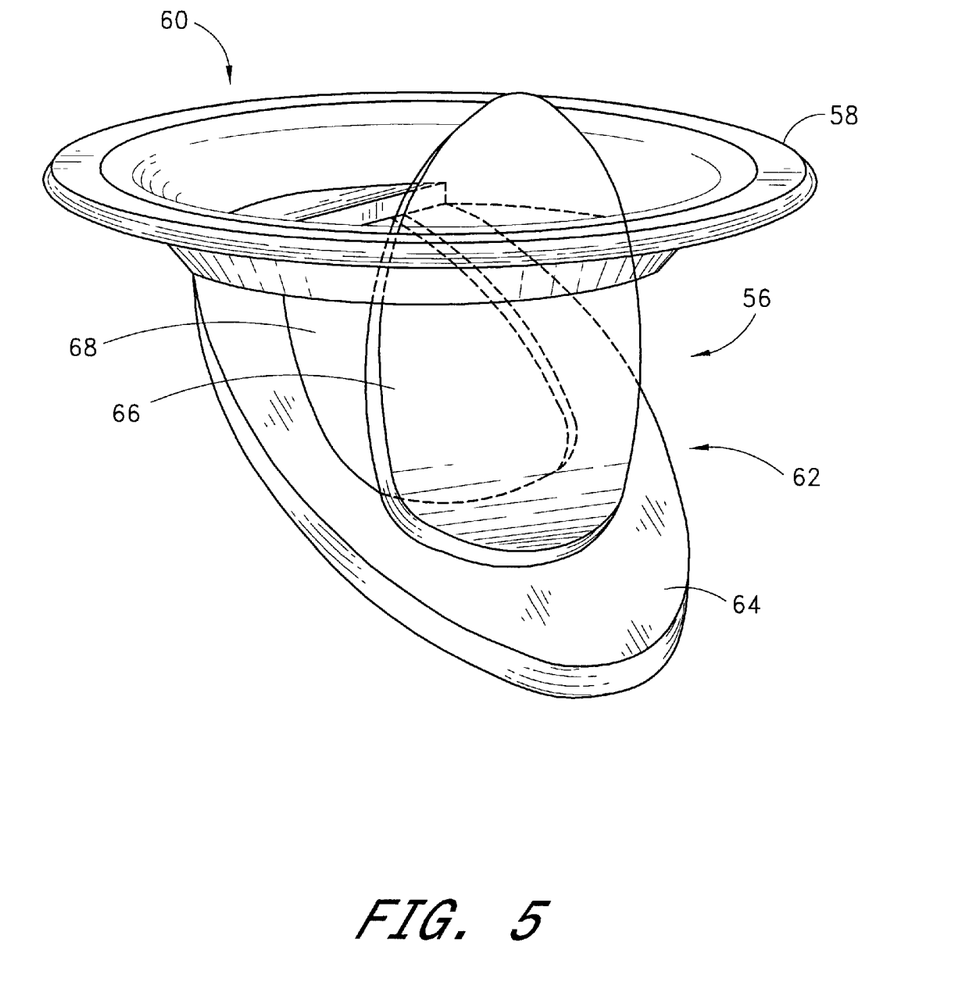
FIG. 5 is a side elevational perspective view of a further alternate gastroesophageal valve in accordance with the present invention.

Referring to FIG. 5, there is illustrated a further embodiment of a valve useful in the present invention. The valve 56 comprises an annular attachment ring 58 having a central aperture 60 therethrough. A compound flapper 62 comprises a forward flow component 64 and a reverse flow component 66. Forward flow is accomplished by displacing both the reverse flow component 66 and forward flow component 64 in a distal direction, thereby opening central aperture 60 to permit forward flow. Reverse flow is accomplished by seating component 64 against annular ring 58, and permitting reverse flow component 66 to pivot in a proximal direction thereby opening reverse flow path 68.

The valve of FIG. 5 can be integrally molded from suitable biocompatible materials, such as silicone, polyurethane, or other materials known in the art. Alternatively, two or more components can be separately manufactured and assembled together to produce the valve 56. For example, forward flapper component 64 and reverse component 66 can be manufactured as an integral unit and subsequently attached to the proximal ring 58 such as through the use of a pin or other hinged attachment structure. Annular ring 58 may be provided with internal or external support structures, such as an annular wire as has been discussed, to enhance the a structural integrity of the removable connection between the valve 56 and the anchor 18.

Referring to FIG. 3, the valve assembly of FIG. 2 is shown in an exploded fashion, along with a tubular support 40 for use during cellular ingrowth into and/or through the wall of the anchor 18. In general, the anchor 18 may have relatively little structural integrity, and is desirably held in place against the esophageal wall for a sufficient period of time to permit cellular ingrowth. In one embodiment, the tubular support 40 is thereafter removable such as by radial compression, and retraction into a retrieval catheter. Depending upon the construction of tubular support 40, the support 40 may alternatively be disassembled and withdrawn into a retrieval device. As a further alternative, the tubular support 40 is constructed of a bioabsorbable material, such that the tubular support 40 dissolves or is otherwise disintegrated after a suitable ingrowth period of time. Absorption or disintegration of the self removable embodiment may occur as a function of the passage of time in the intended use environment, or may be catalyzed or facilitated such as by the application of an activating agent which initiates or accelerates degradation of the material of the tubular support 40. The use of a tubular support 40 may not be necessary, however, in an embodiment in which the anchor 18 is tacked, sutured, or otherwise mechanically secured to the esophageal wall.

Tubular support 40 preferably comprises an elongate self-expandable tubular wire cage, adapted to be compressed into a relatively low cross-sectional profile such as for implantation and capable of self-expansion upon release from a deployment device within the anchor 18 at the attachment site. One example of a self-expandable tubular support which may be adapted for use in the present invention is that disclosed in U.S. Pat. No. 5,282,824 to Gianturco, entitled Percutaneous Stent Assembly, the disclosure of which is incorporated in its entirety herein by reference. Although the Gianturco structure is disclosed in the context of a coronary stent, this structure may be readily scaled up to suitable dimensions for use in the lower esophagus as will be apparent to those of skill in the art in view of the disclosure herein.

Any of a variety of alternate structures can be utilized for tubular support 40. Self-expandable tubular supports can be configured from any of a variety of materials well known in the cardiovascular stent and graft arts, such as the stainless steel and Nitinol. Alternatively, tubular support 40 can be designed for implantation and expansion using an expansion device such as a balloon catheter as will be understood by those of skill in the art.

In one embodiment, the tubular support 40 is additionally provided with a plurality of radially outwardly extendable hooks or barbs, which can be pressed into the mucosal lining to minimize the risk of migration during the cellular ingrowth stage. Expandable tubular wire supports having hooks or barbs to minimize axial migration are disclosed in the context of abdominal aortic aneurism grafts, for example, in U.S. Pat. No. 5,562,728 to Lazarus, et al., the disclosure of which is incorporated in its entirety herein by reference. Attachment barbs may be adapted to extend radially outwardly into the esophageal mucosa automatically upon expansion of the tubular support 40. Alternatively, the attachment barbs may be radially outwardly advanceable in response to manipulation of a control or manually exerted pressure from a tacking device, graspers or other tool which may be transesophageally positioned within the tubular support 40, such as through the working channel of an endoscope.

Figure 6:
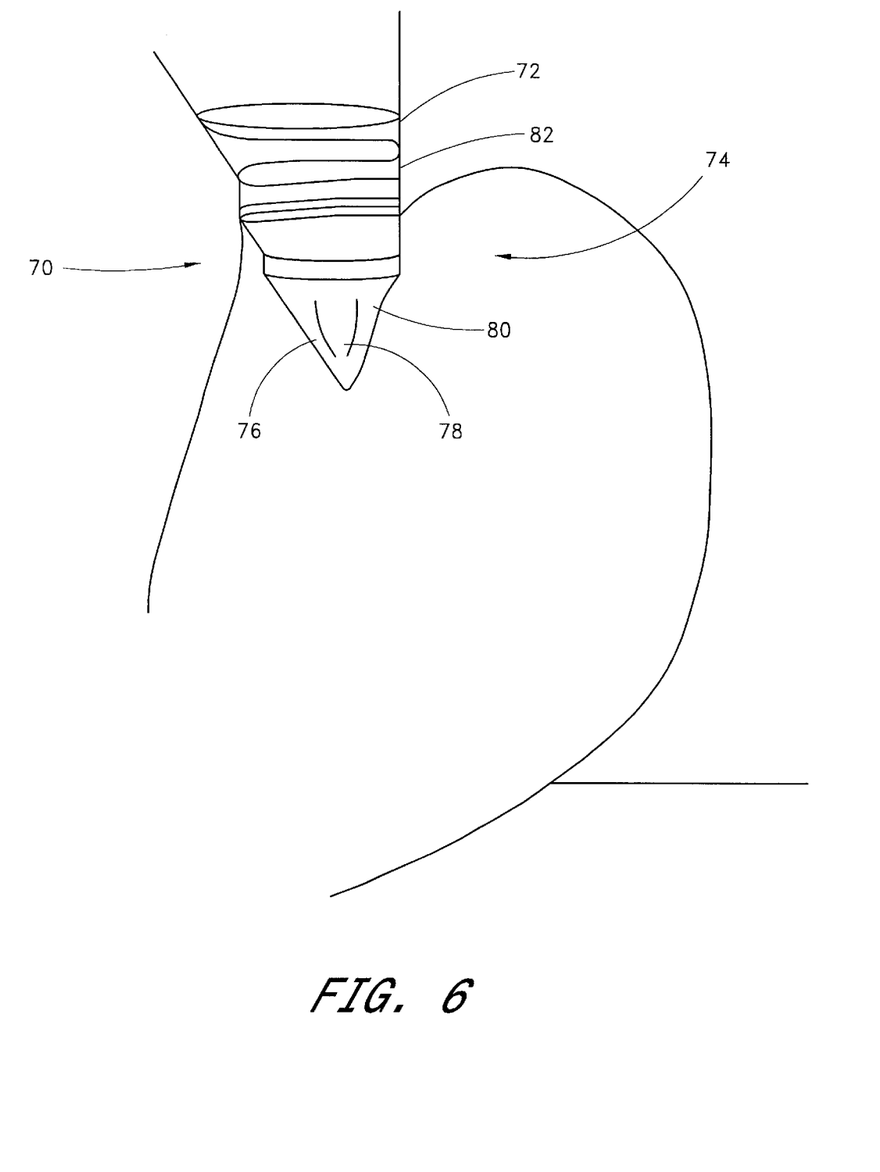
FIG. 6 is a schematic representation of an alternate embodiment of the present invention.

Referring to FIG. 6, there is disclosed an alternate embodiment of the present invention. A prosthetic LES valve 70 generally comprises a support 72, connected to a valve 74. Support 72 comprises a radially expandable support structure such as a wire mesh or wire coil such as may be adapted from the coronary artery stent or abdominal aortic aneurysm graft arts. The wire coil may comprise any of a variety of materials, such as stainless steel, which may be radially expanded following deployment from a tubular catheter. Alternatively, memory metals such as Nitinol may be utilized as will be understood by those of skill in the art.

Valve 74 may comprise any of a variety of valves previously disclosed herein. In the illustrated embodiment, Valve 74 comprises a three leaflet valve, having a first coaptive leaflet 76, a second coaptive leaflet 78 and a third coaptive leaflet 80. Three leaflet valves are well understood in the heart valve arts, and can be used on the embodiment of FIG. 6 or any other embodiment disclosed herein.

Preferably, the support 72 such as a coil stent is surrounded by an outer tubular sleeve 82. Outer sleeve 82 provides a tissue ingrowth surface thereon, and may comprise materials disclosed elsewhere herein such as porous PTFE or Dacron.

In accordance with one implantation method of the present invention, the lower esophageal wall and/or cardia is denuded or injured such as by the use of a mechanical abrasion device and/or chemical exposure. Bipolar or monopolar radio frequency electrodes (e.g. electrocautery) may also be utilized to injure the esophageal lining. In general, the esophageal wall in the lower esophagus is in the area of 3 to 4 mm thick. Preferably, the mucosal layer is injured or removed down to a depth sufficient to ensure adequate ingrowth into the anchor 18.

The valve assembly 16 including a self-expandable tubular support 40 is preferably preloaded into a tubular introducer. In general, the introducer comprises an elongate tubular body preferably having an outside diameter of no more than about 5 to about 15 mm or smaller. The valve assembly 16 is preferably radially compressed within the central lumen of the tubular introducer, such as at the point of manufacture. The valve assembly 16 may include the valve 20, for deployment in a single operation. Alternatively, the introducer may be preloaded with the anchor 18 and self expandable tubular support 40 for deployment in a first step, with the valve 20 to be subsequently deployed within the releasable connector 28 of the previously implanted anchor 18 as a second step. The tubular introducer comprises an axially moveable platform which may be distally advanced within the tubular housing to deploy the valve assembly 16 therefrom. The introducer is advanced transesophageally (or laparoscopically or percutaneously) to the deployment site, and the valve assembly and tubular support 40 are deployed. Upon deployment of the tubular support from the deployment device, the tubular support 40 radially outwardly expands to compress the anchor 18 against the esophageal wall.

Following deployment of the valve assembly 16 at the attachment site, the tubular support 40 may be left in place for a sufficient ingrowth period of time and then removed from the patient. The inventor contemplates removal of the tubular support within the range of from about 2 to 6 weeks following implantation. Alternatively, the tubular support may be left in place within the anchor 18.

As will be appreciated in view of the foregoing removable valve disclosure, the valve 20 may be removed from the anchor 18 while leaving the anchor 18 in position within the esophagus. This may be accomplished, for example, by retracting the valve 20 within a tubular sheath positioned transesophageally within the anchor 18. A replacement valve may thereafter be deployed within the releasable connector 28. The anchor 18 may also be removed, if desired, such as by ablation or denuding of the ingrown tissue using chemical, electrical or mechanical abrading techniques. Alternatively, the anchor 18 may be excised from the esophageal wall such as by cutting with any of a variety of cutting tools adaptable for use through the working channel of an endoscope.

Although the foregoing invention has been disclosed in terms of certain preferred embodiments, other specific embodiments can be constructed in view of the disclosure herein without departing from the spirit and scope of the present invention. Accordingly, the scope of applicant's invention is to be determined by reference to the attached claims, which are not limited to any of the particular embodiments disclosed herein.

What is claimed is:

1. A method of treating gastroesophageal reflux disease, comprising the steps of:
   providing a prosthetic gastroesophageal valve having an anchor and a valve releasable attached to the anchor;
   positioning the valve assembly at about the base of the esophagus;
   contacting the anchor to the wall of the esophagus or cardia to permit cellular ingrowth through the wall of the anchor.

2. A method as in claim 1, further comprising the step of expanding a tubular support within the anchor, to press the anchor against the adjacent tissue.

3. A method as in claim 2, further comprising the step of removing the tubular support from the anchor following a cellular ingrowth period of time.

4. A method as in claim 1, further comprising the step of removing the valve from the anchor while leaving the anchor in place within the esophagus.

5. A method of attaching a prosthesis to the esophagus or cardia, comprising the steps of:
   providing a prosthesis having at least one cellular ingrowth surface thereon;
   preparing a surface of the wall of the esophagus or cardia for attachment to the cellular ingrowth surface by mechanically abrading tissue from the surface of the wall of the esophagus;
   contacting the cellular ingrowth surface to the prepared surface, and
   permitting cellular ingrowth from the prepared surface into the cellular ingrowth surface to attach the prosthesis to the prepared surface.

6. A method of attaching a prosthesis to the esophagus or cardia, comprising the steps of:
   providing a prosthesis having at least one cellular ingrowth surface thereon;
   preparing a surface of the wall of the esophagus or cardia for attachment to the cellular ingrowth surface by contacting a chemical to the surface of the wall of the esophagus;
   contacting the cellular ingrowth surface to the prepared surface, and permitting cellular ingrowth from the prepared surface into the cellular ingrowth surface to attach the prosthesis to the prepared surface.

7. A method as in claim 5, wherein the prosthesis comprises a valve.

8. A method as in claim 7, wherein the valve is permanently attached to the cellular ingrowth surface.

9. A method as in claim 7, wherein the valve is removably attached to the cellular ingrowth surface.

10. A method as in claim 5, wherein the cellular ingrowth surface comprises a porous material.

11. A method as in claim 10, wherein the material comprises PTFE.

12. A method as in claim 5, wherein the contacting step fuirther comprises positioning an expandable support within the esophagus to press the cellular ingrowth surface against the wall of the esophagus.

13. A method as in claim 12, wherein the permitting step comprises leaving the support in position for at least a cellular ingrowth period.

14. A method as in claim 13, wherein the period is between about 1 and 45 days.

15. A method as in claim 5, wherein the prosthesis comprises a flexible, porous, tubular sleeve.

16. A method as in claim 5, wherein the preparing the surface step comprises injuring a portion of the surface of the cardia.

* * * * *

UNITED STATES PATENT AND TRADEMARK OFFICE
CERTIFICATE OF CORRECTION

PATENT NO.   : 6,264,700 B1  
DATED        : July 24, 2001  
INVENTOR(S)  : John Kilcoyne et al.

It is certified that error appears in the above-identified patent and that said Letters Patent is hereby corrected as shown below:

Column 10,
Line 59, please change "releasable" to -- releasably --

Signed and Sealed this

Fourth Day of June, 2002

*Attest:*

*Attesting Officer*

JAMES E. ROGAN
*Director of the United States Patent and Trademark Office*